United States Patent
Kim et al.

(10) Patent No.: US 11,773,417 B2
(45) Date of Patent: Oct. 3, 2023

(54) **MICROALGAL STRAINS OF *THRAUSTOCHYTRIUM* GENUS, AND METHOD OF PRODUCING POLYUNSATURATED FATTY ACIDS USING THE SAME**

(71) Applicant: CJ CHEILJEDANG CORPORATION, Seoul (KR)

(72) Inventors: Ji Young Kim, Seoul (KR); Myung Geun Park, Seoul (KR); Hye Min Park, Seoul (KR); Jung Woon Choi, Seoul (KR); Sang Min Park, Seoul (KR); Sang Young Bae, Seoul (KR); Jin Sook Chang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 219 days.

(21) Appl. No.: 16/971,713

(22) PCT Filed: Jun. 26, 2019

(86) PCT No.: PCT/KR2019/007697
§ 371 (c)(1),
(2) Date: Aug. 21, 2020

(87) PCT Pub. No.: WO2020/004924
PCT Pub. Date: Jan. 2, 2020

(65) Prior Publication Data
US 2021/0002680 A1 Jan. 7, 2021

(30) Foreign Application Priority Data
Jun. 29, 2018 (KR) .................. 10-2018-0075945

(51) Int. Cl.
*C12P 7/64* (2022.01)
*C12N 1/12* (2006.01)
*C12R 1/89* (2006.01)

(52) U.S. Cl.
CPC .................. *C12P 7/64* (2013.01); *C12N 1/12* (2013.01); *C12N 1/125* (2021.05); *C12R 2001/89* (2021.05)

(58) Field of Classification Search
CPC ......... C12P 7/64; C12P 7/6436; C12P 7/6427; C12N 1/12; C12N 1/125; C12N 1/00; C12R 2001/89; Y02E 50/30
See application file for complete search history.

(56) References Cited

U.S. PATENT DOCUMENTS

2018/0179560 A1 6/2018 Ugalde et al.

FOREIGN PATENT DOCUMENTS

| JP | 2017-518747 A | 7/2017 | |
|---|---|---|---|
| KR | 10-2007-0040751 A | 4/2007 | |
| KR | 10-2015-0084148 A | 7/2015 | |
| KR | 10-2016-0098233 A | 8/2016 | |
| WO | WO 2015/179844 A2 * | 5/2015 | ............... C12P 7/64 |

OTHER PUBLICATIONS

Sun et al (Differential effects of nutrient limitations on biochemical constituents and docosahexaenoic acid production of *Schizochytrium* sp.—Bioresource Technology 159, pp. 199-206 (Year: 2014).*
Cakmak et al (Differential Effects of Nitrogen and Sulfur Deprivation on Growth and Biodiesel Feedstock Production of Chlamydomonas reinhardtii—Biotechnology and Bioengineering, vol. 109, No. 8, pp. 1947-1957 (Year: 2012).*
Frenz et al., "Hydrocarbon recovery by extraction with a biocompatible solvent from free and immobilized cultures of Botryococcus braunii," Enzyme Microbial Technology, 11: 717-724 (1989).
Sawayama et al., "Possibility of renewable energy production and CO2 mitigation by thermochemical liquefaction of microalgae," Biomass and Bioenergy 17: 33-39 (1999).
Inoue et al., "Analysis of Oil Derived from Liquefaction of Botryococcus Braunii," Biomass Bioenergy 6 (4): 269-274 (1994).
Minowa et al., "Oil production from algal cells of Dunaliella tertiolecta by direct thermochemical liquefaction," Fuel 74 (12): 1735-1738 (1995).
Mendes et al., "Supercritical carbon dioxide extraction of compounds with pharmaceutical importance from microalgae," Inorganica Chimica Acta 356: 328-334 (2003).
Miao et al., "Biodiesel production from heterotrophic microalgal oil," Biosource Technology 97: 841-846 (2006).
Yang et al., "Isolation and Characterization of Taiwanese Heterotrophic Microalgae: Screening of Strains for Docosahexaenoic Acid (DHA) Production," Marine Biotechnology, 12: 173-185 (2010).
Furlan et al., "Production of Docosahexaenoic Acid (DHA) from *Thraustochytrium* sp. ATCC 26185 Using Differents Nitrogen Concentrations," B.Ceppa 32 (1): 1-10 (2014).
International Search Report issued in corresponding International Patent Application No. PCT/KR2019/007697 dated Oct. 2, 2019.

\* cited by examiner

*Primary Examiner* — Ganapathirama Raghu
(74) *Attorney, Agent, or Firm* — Morgan, Lewis & Bockius LLP

(57) ABSTRACT

The present disclosure relates to strains of *Thraustochytrium* genus, including a high content of polyunsaturated fatty acids, and a method of producing a biomass using the same. According to the novel CJM01 microalgae of *Thraustochytrium* genus of the present disclosure, the content of lipids in the biomass and the content of unsaturated fatty acid such as docosahexaenoic acid in the biomass are high, so that the microalgae itself, a biomass produced by the culturing and fermentation of microalgae, a condensate of the biomass, and a dried product of the biomass are very useful as a feed composition.

9 Claims, 1 Drawing Sheet
Specification includes a Sequence Listing.

SEQUENCE LISTING

<160> NUMBER OF SEQ ID NOS: 3

<210> SEQ ID NO 1
<211> LENGTH: 1792
<212> TYPE: DNA
<213> ORGANISM: Unknown
<220> FEATURE:
<223> OTHER INFORMATION: Thraustochytrium sp.

<400> SEQUENCE: 1

```
aacctggttg atcctgccag tagtcatacg cttatctcaa agattaagcc atgcatgtct    60
aagtataaag gcttatactc tgaaactgcg aacggctcat tatatcagtt atagtttctt   120
tgatagtgtt ttttctacat ggatacttgt ggcaaatcta gaaacaatac atgcgtacag   180
gcctgacttt gggggagggc tgcatttatt tgacttaagc caatacccct cggggttgtt   240
ttggtgattc agaataactg agcgaatcgc atagctttcg ggcggcgatg aatcattcaa   300
gtttctgccc catcagctgt cgatggtagg gtataggcct accatggctg tcacgggtga   360
cggagaatta gggttcgatt ccggagaggg agcctgagag acggctacca catccaagga   420
aggcagcagg cgcgtaaatt actcaatgtt gactcgacga agtagtgacg agaattaaca   480
atgcggagcg ctacgcgttt tgcaattgga atgagagcaa tgtaaaagcc tcatcgagga   540
tccattggag ggcaagtctg gtgccagcag ccgcggtaat tccagctcca atagcgtata   600
ctaaagttgt tgcagttaaa agctcgtag ttgaacctct ggtagggccg accttggcgc   660
gcggtgaatg ccgcggtgct tgaaagcgtc gttgcccggc catcctcccc cggtcttttg   720
ggctgggggt cgtttactgt aaaaaaaata gagtgttcca agcaggggt aatgtcccgg   780
tatatagtag tatggaataa tgagatagga ctttggtact attttgttgg tttgcatgcc   840
aaggtaatga ttaagaggga cagttggggg tattcgtatt tagatgtcag aggtgaaatt   900
cttggatttt cgaaagacga actactgcga aagcatttac caaggatgtt ttcattaatc   960
aagaacgaaa gttagggat cgaagatgat tagataccat cgtagtctta accgtaaact  1020
atgccgactt gcgattgtcc ggcgtcgctt ttagatgacc tgggcagcag cacatgagaa  1080
atcaaagtct ttgggttccg gggggagtat ggtcgcaagg ctgaaactta aaggaattga  1140
cggaagggca ccaccaggag tggagcctgc ggcttaattt gactcaacac gggaaaactt  1200
accaggtccg gacataggaa ggattgacag attgagagct cttctcttgat tctatgggtg  1260
gtggtgcatg gccgttctta gttggtggag tgatttgtct ggttaattcc gttaacgaac  1320
gagaccacag cctactaaat agtggccgtt atggcgacat agcggtgaac ttcttagagg  1380
gacatttcgg gtataccgga aggaagtttg tgcaataac aggtctgtga tgcccttaga  1440
tgttctgggc cgcacgcgcg ctacactgat cggttcaacg agtatttgtt gttttttcccg  1500
ttttgggagg gggcagagtc cttggccgga aggtctgggt aatcttttga atgccgatcg  1560
tgatggggct agattttttgc aattattaat ctccaacgag gaattcctag tagacgcaag  1620
tcatcagctt gcatcgatta cgtccctgcc ctttgtacac accgcccgtc gcacctaccg  1680
attgaacgat ccggtgagac cttgggattc tgttgtggct gattaatttt ggctgcgatg  1740
ggagaacttg agcaaacctt atcgtttaga ggaaggtgaa gtcgtaacaa gg           1792
```

<210> SEQ ID NO 2
<211> LENGTH: 22
<212> TYPE: DNA
<213> ORGANISM: Artificial Sequence
<220> FEATURE:
<223> OTHER INFORMATION: 18s-001F

<400> SEQUENCE: 2

```
aacctggttg atcctgccag ta                                              22
```

<210> SEQ ID NO 3
<211> LENGTH: 25
<212> TYPE: DNA

```
<213> ORGANISM: Artificial Sequence
<220> FEATURE:
<223> OTHER INFORMATION: 18s-013R

<400> SEQUENCE: 3
ccttgttacg acttcacctt cctct                                              25
```

MICROALGAL STRAINS OF *THRAUSTOCHYTRIUM* GENUS, AND METHOD OF PRODUCING POLYUNSATURATED FATTY ACIDS USING THE SAME

SEQUENCE LISTING SUBMISSION VIA EFS-WEB

A computer readable text file, entitled "SequenceListing.txt," created on or about Sep. 10, 2020 with a file size of about 3 kb contains the sequence listing for this application and is hereby incorporated by reference in its entirety.

TECHNICAL FIELD

The present disclosure relates to strains of *Thraustochytrium* genus, including a high content of polyunsaturated fatty acids, a biomass produced from the strains, a lipid including the strains, and a method of producing polyunsaturated fatty acids.

BACKGROUND ART

Docosahexaenoic acid (DHA), which is a polyunsaturated fatty acid, is a fatty acid essential for brain, eye tissues and nervous systems, and is known to play an important role in the development of visual acuity and motor neuron ability of infants. It was reported that the amount of DHA is significantly reduced in the brain of a dementia patient, and it is newly discovered that DHA has various anti-aging functions such as suppression of macular degeneration in presbyopia. Further, it was reported that DHA can also be used as a feed additive for fish (Korean Patent Application Publication No. 10-2007-0040751). Since most higher animals, including humans, cannot smoothly synthesize polyunsaturated fatty acids required for nominal biological functions, they must ingest polyunsaturated fatty acids as essential nutrients, and the World Health Organization recommends a steady consumption of DHA-containing polyunsaturated fatty acids at least 1 g/day. Traditionally, the supply sources of DHA polyunsaturated fatty acids are deep sea fish such as tuna and salmon which occupy the top level of the marine ecosystem. However, as the pollution of the marine environment becomes worse, the risk of ingestion of deep sea fish is increasing due to the accumulation of pollutants such as mercury, heavy metals, environmental hormones and radioactive substances in the body of deep sea fish. Therefore, as new means to safely and reliably supply DHA polyunsaturated fatty acid oil, microalgae of *Thraustochytrium* genus have very important industrial values.

Various methods for gene overexpression have been suggested in microalgae of *Thraustochytrium* genus. Transformation technologies of microalgae of *Thraustochytrium* genus using various antibiotic resistance genes as selection markers were reported since genetic transformation methods of microalgae of *Thraustochytrium* genus using acetolactate synthase as a selection marker was first introduced by Martec Corporation. Specifically, Korean Patent Application Publication No. 2015-0084148 discloses "a recombinant vector for increasing the productivity of microalgal biomass and lipid and a use thereof".

However, up to now, a genetic transformation technology developed from microalgae of *Thraustochytrium* genus is a chromosomal integration method in which genes introduced in common are inserted into chromosomal DNA, and has an advantage of the inserted genes being stably maintained, but has limitations in gene copy number and expression control as compared with a gene expression method using centromeric or episomal plasmid with self-replication ability.

DISCLOSURE

Technical Problem

Accordingly, the present inventors have developed microalgae having improved the content and productivity of docosahexaenoic acid by mutating KC01 microalgae of *Thraustochytrium* genus, and have established a biomass including a docosahexaenoic acid-containing lipid and a method of producing a bio-oil by culturing these microalgae. Based on these development and establishment, the present disclosure has been completed.

Technical Solution

One object of the present disclosure is to provide CJM01 microalgae (deposit number: KCTC 13538BP) of *Thraustochytrium* genus by which the production of docosahexaenoic acid (DHA) increases and the production of amino acid decreases as compared with wild microalgae.

Another object of the present disclosure is to provide a method of producing a biomass, including steps of culturing CJM01 microalgae of *Thraustochytrium* genus; and recovering a biomass containing docosahexaenoic acid (DHA) from the microalgae, a cultured product thereof, a dried product thereof, or a pulverized product thereof.

Still another object of the present disclosure is to provide a method of producing a bio-oil, including steps of: culturing CJM01 microalgae of *Thraustochytrium* genus; and recovering a lipid containing docosahexaenoic acid (DHA) from the microalgae, a cultured product thereof, a dried product thereof, or a pulverized product thereof.

Advantageous Effects

According to the novel CJM01 microalgae of *Thraustochytrium* genus of the present disclosure, the production of an amino acid is remarkably reduced, and the content of a fat in biomass and the content of an unsaturated fatty acid such as docosahexaenoic acid are high, so that the microalgae itself, biomass produced by the culturing and fermentation of microalgae, a condensate of the biomass, and a dried product of the biomass are very useful as a feed composition.

BEST MODE FOR INVENTION

Figure 1:
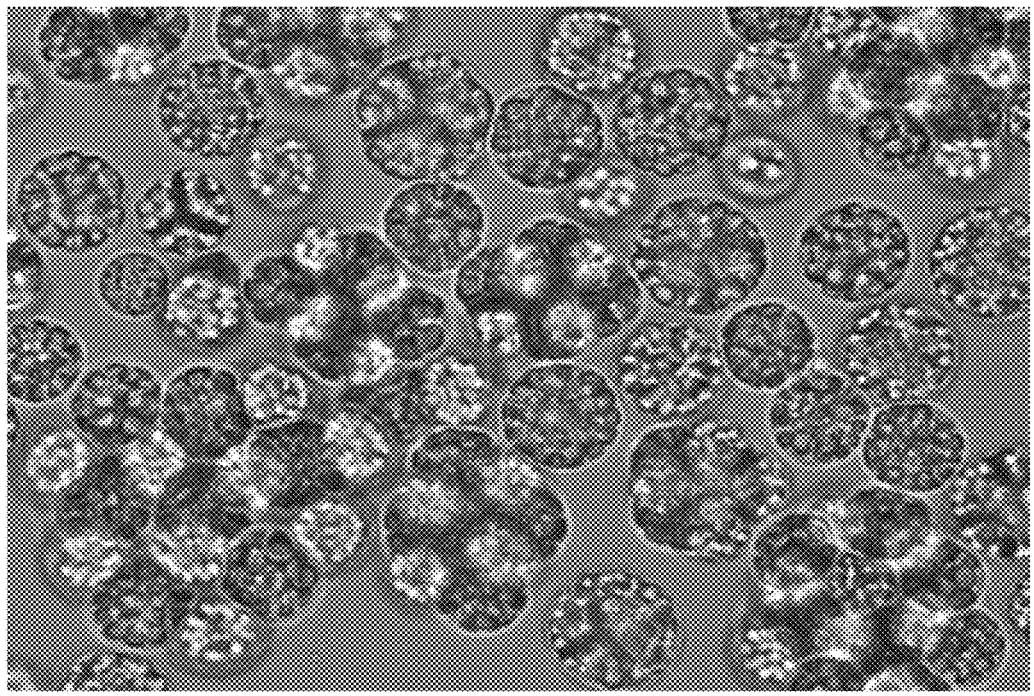
FIG. 1 is a photograph showing KC01 strains of *Thraustochytrium* genus observed by an optical microscope.

Hereinafter, the present disclosure will be described in detail.

Meanwhile, specific structural and functional descriptions of embodiments disclosed herein are only for illustrative purposes of other embodiments. The present disclosure may be embodied in many different forms without departing from the spirit and significant characteristics of the present disclosure. Therefore, the embodiments of the present disclosure are disclosed only for illustrative purposes and should not be construed as limiting the present disclosure.

In order to accomplish the above objects, an aspect of the present disclosure provides CJM01 microalgae of *Thraustochytrium* genus by which the production of docosahexaenoic acid (DHA) increases and the production of amino acid decreases, as compared with wild microalgae.

As used herein, the term "strains of *Thraustochytrium* genus" refers to organic heterotrophic microalgae, which play an important role as supply sources of triacylglycerol containing various polyunsaturated fatty acids including docosahexaenoic acid (DHA) at a high concentration. Further, the "microalgae" refer to living organisms that can be seen only through a microscope because it cannot be seen by the naked eye and that floats freely in water, and are also called phytoplankton.

As used herein, for example, wild KC01 strains of *Thraustochytrium* genus are irradiated with gamma rays to generate mutant strains, strains having improved productivity of oil containing polyunsaturated acids are selected from the mutant strains, and these strains were named as CJM01 strains of *Thraustochytrium* genus, deposited on May 30, 2018 with the Korean Collection for Type Cultures (KCTC), an international depository organization under the Budapest Treaty, and granted the deposit number KCTC 13538BP.

Further, the CJM01 microalgae of *Thraustochytrium* genus of the present disclosure may have a 18s rRNA of SEQ ID NO. 1, but the present disclosure is not limited thereto.

As used herein, the term "docosahexaenoic acid (DHA)" is one of polyunsaturated fatty acids represented by Formula $C_{22}H_{32}O_2$, and is a material extracted extensively from blue fish such as tuna or sardine. Further, docosahexaenoic acid (DHA) belongs to omega 3 together with eicosapentaenoic acid (EPA) and α-linolenic acid (ALA).

The CJM01 microalgae of *Thraustochytrium* genus of the present disclosure may include a large amount of docosahexaenoic acid (DHA), as compared with the KC01 strains of *Thraustochytrium* genus which are parent strains. Specifically, the CJM01 microalgae may include docosahexaenoic acid (DHA) in an amount of 30 wt % to 65 wt %, 30 wt % to 60 wt %, 40 wt % to 65 wt %, or 40 wt % to 60 wt %, based on the total weight of fatty acids included in the microalgae, but the present disclosure is not limited thereto.

Additionally, the CJM01 microalgae of *Thraustochytrium* genus of the present disclosure may have improved docosahexaenoic acid (DHA) productivity, as compared with the KC01 strains of *Thraustochytrium* genus which are parent strains. The docosahexaenoic acid (DHA) productivity may be measured by the concentration (g/L) of docosahexaenoic acid (DHA) produced for 1 hour. The microalgae of the present disclosure may have a docosahexaenoic acid (DHA) productivity of 0.4 to 0.8 (g/l/h), 0.4 to 0.7 (g/l/h), 0.5 to 0.8 (g/l/h), or 0.5 to 0.7 (g/l/h), but the present disclosure is not limited thereto.

Meanwhile, in the CJM01 microalgae of *Thraustochytrium* genus of the present disclosure, the production of an amino acid may be reduced, as compared with the KC01 strains of *Thraustochytrium* genus which are parent strains. Specifically, the CJM01 microalgae of *Thraustochytrium* genus of the present disclosure or a culture solution thereof may not include at least one amino acid selected from the group consisting of aspartate, serine, glutamate, glycine, alanine, valine, methionine, isoleucine, leucine, tyrosine, phenylalanine, lysine, and arginine. For example, as can be seen in Example 2, aspartate, serine, glutamate, glycine, alanine, valine, methionine, isoleucine, leucine, tyrosine, phenylalanine, lysine, and arginine may not be detected from the culture solution of the CJM01 microalgae of *Thraustochytrium* genus of the present disclosure.

For example, the total production of an amino acid by the CJM01 microalgae of *Thraustochytrium* genus of the present disclosure may be reduced by 90% or more, 95% or more, 97% or more, or 99% or more, as compared with the KC01 strains of *Thraustochytrium* genus which are parent strains. This indicates that the CJM01 strains are more effectively used in the pathway of docosahexaenoic acid biosynthesis as compared with the KC01 parent strains. Specifically, since the CJM01 microalgae of *Thraustochytrium* genus of the present disclosure rarely produce amino acids, the culture solution of the strains may include amino acids only in an amount of 0.1 to 20 mg/L, 0.1 to 15 mg/L, 0.1 to 10 mg/L, 0.1 to 7 mg/L, or 0.1 to 5 mg/L.

Another aspect of the present disclosure provides a method of producing a biomass, including: culturing CJM01 microalgae of *Thraustochytrium* genus; and recovering a biomass containing docosahexaenoic acid (DHA) from the microalgae, a cultured product thereof, a dried product thereof, or a pulverized product thereof. Further, the biomass may be made in the form of a dry fungus body, but the present disclosure is not limited thereto.

The present disclosure provides a biomass produced by the method. The biomass may include docosahexaenoic acid (DHA) in an amount of 15 to 40 wt %, 20 to 35 wt %, or 25 to 30 wt %, based on the total weight thereof, but the present disclosure is not limited thereto.

A still another aspect of the present disclosure provides a method of producing a bio-oil, including: culturing CJM01 microalgae of *Thraustochytrium* genus; and recovering a lipid containing docosahexaenoic acid (DHA) from the microalgae, a cultured product thereof, a dried product thereof, or a pulverized product thereof.

The present disclosure provides a bio-oil produced by the method. The bio-oil may include docosahexaenoic acid (DHA) in an amount of 30 to 65 wt %, 30 to 60 wt %, 40 to 65 wt %, or 40 to 60 wt %, based on the total weight of fatty acids, but the present disclosure is not limited thereto.

Specifically, the method of producing a bio-oil according to the present disclosure may include steps of culturing the CJM01 microalgae of *Thraustochytrium* genus; producing a biomass containing docosahexaenoic acid (DHA) from the microalgae, a cultured product thereof, a dried product thereof, or a pulverized product thereof, and recovering a lipid containing docosahexaenoic acid (DHA) from the produced biomass. However, the present disclosure is not limited thereto.

The "*Thraustochytrium* genus" and "docosahexaenoic acid" are as described above.

As used herein, the "bio-oil" is obtained from a biomass by a biological, thermochemical, or physiochemical extraction process. The bio-oil produced according to the present disclosure may include polyunsaturated fatty acid, specifically, docosahexaenoic acid, but the present disclosure is not limited thereto.

Additionally, the "biomass" refers to organisms such as plants, animals and microorganisms that can be used as chemical energy, that is, energy sources of bio-energy. In addition, the biomass ecologically also refers to the weight or energy amount of a specific organism exiting within unit time and space. Further, although the biomass includes compounds secreted by cells, it may also include extracellular materials as well as cells and/or intracellular contents. As used herein, the biomass may be the CJM01 microalgae itself of *Thraustochytrium* genus, a cultured product thereof, a dried product thereof, a pulverized product thereof, a product produced by culturing or fermenting the microalgae, or may be a condensate of the biomass or a dried product of the biomass. However, the biomass is not limited thereto.

As used herein, the cultured product of the CJM01 microalgae of *Thraustochytrium* genus refers to a product obtained by culturing the microalgae, and specifically, may be a culture solution including the microalgae or a culture solution not including the microalgae, but the present disclosure is not limited thereto. As used herein, the cultured product of the CJM01 microalgae of *Thraustochytrium* genus refers to a product obtained by removing moisture from the microalgae, and specifically, may be made in the form of a dry fungus body, but the present disclosure is not limited thereto. As used herein, the pulverized product of the CJM01 microalgae of *Thraustochytrium* genus collectively refers to a product obtained by pulverizing the microalgae, and may be made in the form of supernatant or pellet, but the present disclosure is not limited thereto.

The CJM01 microalgae itself of *Thraustochytrium* genus, the cultured product thereof, the dried product thereof, or the pulverized product thereof includes docosahexaenoic acid, and may be used to produce a biomass or a bio-oil.

As used herein, the term "culturing" means that the microalgae are grown under moderately controlled environmental conditions. The culturing process according to the present disclosure may be performed depending on appropriate culture medium and culturing conditions. Such a culturing process may be easily adjusted by those skilled in the art according to the selected microalgae.

Specifically, the culturing of the CJM01 microalgae of *Thraustochytrium* genus according to the present disclosure may be performed under heterotrophic conditions, but the present disclosure is not limited thereto.

As used herein, the "heterotrophic nutrition" is a nutritional form that depends on organic matter obtained from in-vitro energy (nutrition) source, and is a term corresponding to independent nutrition. The CJM01 microalgae of *Thraustochytrium* genus according to the present disclosure can improve the amount and productivity of docosahexaenoic acid by optimizing the composition of a culture medium of a carbon source or a nitrogen source under heterotrophic conditions. Further, as used herein, the term "heterotrophic nutrition" may be used interchangeably with "dark culture".

Additionally, the step of culturing the microalgae is not particularly limited, and may be performed by a known batch culture method, a known continuous culture method, a fed-batch culture method, or the like. The culture medium and other culture conditions used in culturing the microalgae of the present disclosure may be used without limitations as long as they can be generally used to culture the microalgae. Specifically, the microalgae of the present disclosure may be cultured in a general culture medium including a carbon source, a nitrogen source, a phosphorus source, an inorganic compound, amino acids, and/or vitamins while adjusting temperature, pH, and the like under aerobic conditions.

Specifically, an optimum pH (for example, a pH of 5 to 9, specifically a pH of 6 to 8, and most specifically a pH of 6.8) may be adjusted by using a basic compound (for example, sodium hydroxide, potassium hydroxide, or ammonia) or an acidic compound (for example, a phosphoric acid or a sulfuric acid), but the present disclosure is not limited thereto.

Further, oxygen or oxygen-containing gas may be injected into a culture to maintain the aerobic state of the culture, or nitrogen gas, hydrogen gas or carbon dioxide gas may be injected into the culture without injecting oxygen or oxygen-containing gas to maintain the anaerobic or non-aerobic state of the culture, but the present disclosure is not limited thereto.

Further, the culturing temperature may be maintained at 20° C. to 45° C., specifically, 25° C. to 40° C., and the culturing may be performed for about 10 to 160 hours, but the present disclosure is not limited thereto. In addition, during the culturing, the formation of bubbles may be inhibited by using a deforming agent such as fatty acid polyglycol ester, but the present disclosure is not limited thereto.

The culturing of the CJM01 microalgae of *Thraustochytrium* genus according to the present disclosure may be performed by using a culture medium including a carbon source and a nitrogen source.

As used herein, the term "culture medium" refers to a medium for culturing the microalgae of the present disclosure and/or a product obtained after culturing the microalgae. The culture medium may have both a form including the microalgae and a form obtained by removing the microalgae from a culture solution including the microalgae through centrifugation, filtration, or the like.

Additionally, in the culture medium used in the present disclosure, as carbon sources, sugars and carbohydrates (for example, glucose, sucrose, lactose, fructose, galactose, mannose, maltose, arabinose, xylose, molasses, starch, and cellulose), fats and oils (soybean oil, sunflower seed oil, peanut oil, and coconut oil), fatty acids (for example, palmitic acid, stearic acid, and linoleic acid), alcohols (for example, glycerol and ethanol), and organic acids (for example, acetic acid) may be used individually or in combination. Specifically, the carbon source may be at least one selected from the group consisting of glucose, fructose, maltose, galactose, mannose, sucrose, arabinose, xylose, and glycerol, but is not limited as long as it can be used to culture microalgae. Further, in the culture medium used in the present disclosure, as the carbon source, glucose having a concentration of 10 to 50 g/L, 10 to 40 g/L, 20 to 50 g/L, 20 to 40 g/L, or 25 to 35 g/L may be used, but the present disclosure is not limited thereto.

The nitrogen sources of the culture medium used in the present disclosure may be classified into organic nitrogen sources and inorganic nitrogen sources, but these organic nitrogen sources and inorganic nitrogen sources may used individually or in combination. Specifically, the nitrogen source may be an organic nitrogen source selected from the group consisting of a yeast extract, a beef extract, peptone, and tryptone, or may be an inorganic nitrogen source selected from the group consisting of ammonium acetate, ammonium nitrate, ammonium chloride, ammonium sulfate, sodium nitrate, urea, and monosodium glutamate (MSG).

Further, in the culture medium used in the present disclosure, examples of the nitrogen source may include a yeast extract, ammonium sulfate, sodium nitrate, and MSG, but are not limited thereto as long as it can be used to culture microalgae.

Specifically, the yeast extract may be included in the culture medium in a concentration of 0.1 to 10 g/L, 0.5 to 10 g/L, 0.5 to 7 g/L, 0.5 to 5 g/L, 0.5 to 3 g/L, 0.5 to 2 g/L, or 0.5 to 1.5 g/L, the ammonium sulfate may be included in the culture medium in a concentration of 1 to 5 g/L, 1 to 4 g/L, 2 to 5 g/L, or 2 to 4 g/L, the sodium nitrate may be included in the culture medium in a concentration of 0.1 to 10 g/L, 0.5 to 9 g/L, 1 to 9 g/L, 2 to 9 g/L, 3 to 9 g/L, 5 to 9 g/L, or 7 to 9 g/L, and the MSG may be included in the culture medium in a concentration of 0.1 to 2 g/L, 0.1 to 1.5 g/L, 0.5 to 2 g/L, or 0.5 to 1.5 g/L. However, the present disclosure is not limited thereto.

For the purpose of the present disclosure, since the CJM01 strains are characterized in that they have no ammonia inhibition and can grow in a wide salt concentration, carbon sources and nitrogen sources may be appropriately adjusted in consideration of these characteristics.

In the culture medium used in the present disclosure, as the phosphorus source, potassium dihydrogenphosphate, dipotassium hydrogenphosphate, and sodium-containing salts corresponding thereto may be used individually or in combination, but the present disclosure is not limited thereto. The culture medium may include other metal salts (for example, magnesium sulfate and iron sulfate), amino acid, and an essential growth-promoting material such as vitamin.

In the step of recovering a biomass from the microalgae cultured in the culturing step, the cultured product thereof, the dried product, or the pulverized product thereof, a desired biomass may be collected by using a suitable method known in the art.

In the step of recovering docosahexaenoic acid produced in the culturing step, desired docosahexaenoic acid may be collected from the microalgae itself or the cultured product thereof by using a suitable method known in the art. For example, a desired biomass or desired docosahexaenoic acid may be recovered from the microalgae cultured by a suitable method known in the art, the cultured product thereof, the dried product thereof, or the pulverized product thereof, and, in this case, centrifugation, filtration, anion exchange chromatography, crystallization, HPLC, or the like may be used. The step of recovering the biomass or docosahexaenoic may additionally include a separation step and/or a purification step.

For example, lipids and lipid derivatives such as fatty aldehydes, fatty alcohols and hydrocarbons (for example, alkanes) may be extracted by a hydrophobic solvent such as hexane (Frenz et al. 1989, Enzyme Microb. Technol., 11:717). Lipids and lipid derivatives may also be extracted by using liquefaction (Sawayama et al. 1999, Biomass and Bioenergy 17: 33-39 and Inoue et al. 1993, Biomass Bioenergy 6 (4): 269-274); oil liquefaction (Minowa et al. 1995, Fuel 74 (12): 1735-1738); and supercritical $CO_2$ extraction (Mendes et al. 2003, Inorganica Chimica Acta 356: 328-334). Further, the protocol of known microalgae lipid recovery discloses a method including the steps of i) collecting cells using centrifugation, washing the collected cells with distilled water and then freeze-king the washed cells to obtain cell powder, and pulverizing the obtained cell powder in a mortar and then extracting lipids using n-hexane [Miao and Wu, Biosource Technology (2006) 97:841-846].

Still another aspect of the present disclosure provides a composition including CJM01 microalgae of *Thraustochytrium* genus, a cultured product thereof, a dried product thereof, or a pulverized product thereof. The composition may include a biomass or bio-oil produced using the microalgae.

The CJM01 microalgae of *Thraustochytrium* genus, the cultured product thereof, the dried product thereof, and the pulverized product thereof are as described above. The biomass or bio-oil produced using the microalgae are also as described above. For the purpose of preparing a composition including a high content of docosahexaenoic acid, the microalgae of the present disclosure may be used. The composition may be made in the form of a solution, a powder, or a suspension, but the present disclosure is not limited thereto. More specifically, a food composition, a feed composition, or a feed additive, which includes CJM01 microalgae of *Thraustochytrium* genus, the cultured product thereof, the dried product thereof, or the pulverized product thereof, may be provided.

As used herein, the term "feed" refers to an animal's food for eating, ingesting and digesting, or refers to any suitable natural or artificial diet, one meal, or an ingredient of the one meal. The feed according to the present disclosure, which includes a composition for preventing or treating metabolic diseases as an active ingredient, can be made into various types of feeds known in the art, and specific examples thereof may include concentrated feed, coarse feed, and/or special feed.

As used herein, the term "feed additive" refers to a material that is added to a feed for the purpose of various effects such as nutrient replenishment, weight loss prevention, improvement in digestive utilization of cellulose in feed, oil quality improvement, reproductive disorder prevention, conception rate improvement, and prevention of high-temperature stress in summer. The feed additive of the present disclosure corresponds to a supplementary feed under the feed management law, and may further include mineral preparation such as sodium hydrogencarbonate, bentonite, magnesium oxide, or complex mineral; mineral preparation that is trace mineral such as zinc, copper, cobalt, or selenium; vitamin preparation such as carotene, vitamin E, vitamins A, vitamin D, vitamin E, nicotinic acid, or vitamin B complex; protective amino acid preparation such as methionine or lysine; protective fatty acid preparation such as fatty acid calcium salt; live bacteria preparation such as probiotic bacteria (lactic acid bacteria), yeast cultures, or mold fermentation products; and yeast preparation.

As used herein, the term "food composition" includes all types of foods, such as functional food, nutritional supplement, health food, and food additives. The above food composition may be produced in various forms according to methods commonly known in the art.

The present disclosure provides a method of producing a composition including the biomass or bio-oil. The biomass, bio-oil, and composition are as described above.

In the above method of producing a bio-oil, a bio-oil including a high content of docosahexaenoic acid may be produced by the step of culturing the CJM01 microalgae of *Thraustochytrium* genus, having high productivity of docosahexaenoic acid, in a culture medium including a carbon source of a specific composition and a nitrogen source of a specific composition under heterotrophic conditions.

MODE FOR INVENTION

Hereinafter, the present disclosure will be described in more detail with reference to Examples. However, these Examples are only illustrative the present disclosure, and the scope of the present disclosure is not limited to these Examples.

The CJM01 microalgae of the present disclosure are microalgae belonging to Thraustochytrid family, and have an ability to produce polyunsaturated fatty acids including a high content of docosahexaenoic acid. The CJM01 microalgae of the present disclosure have a DNA nucleotide sequence of the 18S rRNA gene represented by SEQ ID NO. 1, and have a high content of a biomass under heterotrophic conditions, not under growth conditions in light culture.

In the following examples, experimental methods will be described in more detail.

Example 1: Separation of KC01 Microalgae of Thraustochytrid Family

In order to separate the microalgal strains of Thraustochytrid family, the following experiments were carried out.

Specifically, seawater, soil, and leaf environmental samples were collected from 20 coastal areas of Geoje and Tongyeong areas of Gyeongsangnam-do, Korea. Then, the samples were stored in an ice box at 10° C. and carried to a laboratory. The samples were used in a bacteria separation work within 2 to 3 days. These samples were directly smeared on an agar medium, and then Thraustochytrid strains were separated using a liquid pine powder application method. Samples each including a microalgae-like form observed by a microscope were smeared on an IYP culture medium for microbial separation (1 g/L of yeast extract, 1 g/L of peptone, 2 g/L of $MgSO_4 \cdot 7H_2O$, 20 g/L of sea salt, 5.0 mg/L of $H_3BO_3$, 3.0 mg/L of $MnCl_2$, 0.2 mg/L of $CuSO_4$, 0.05 mg/L of $NaMo_4 \cdot 2H_2O$, 0.05 mg/L of $CoSO_4$, 0.7 mg/L of $ZnSO_4 \cdot 7H_2O$, and 15 g/L of agar) to obtain colonies. The obtained colonies were subjected to subculture several times to be purified and separated, and then only strains forming zoosporangia that are typical characteristics of Thraustochytrid microalgae were selected and separated. Environmental samples that cannot be confirmed through microscopic observation were diluted and washed using sterilized sea water having a salinity of 1.5%, and then these samples were sprayed with pine powder and cultured. Microbial communities obtained by culturing under temperature and pH conditions similar to each collection environment were smeared on an IYP culture medium for microbial separation and subcultured to be purified and separated. In this case, an antibiotic cocktail mix solution (0 to 500 mg/L of streptomycin sulfate, 0 to 500 mg/L of ampicillin, 0 to 500 mg/L of penicillin G, and 0 to 500 mg/L of kanamycin sulfate) was introduced while adjusting the concentration thereof, and thus the growth and pollution of other microbes were controlled.

The separated colonies were cultured in a 500 mL flask at a temperature of 15° C. to 28° C. and a rotation speed of 50 to 200 rpm for about 7 days using an IGGYP culture medium (glycerol 10 g/L, glucose 10 g/L, yeast extract 1 g/L, peptone 1 g/L, $MgSO_4 \cdot 7H_2O$ 2 g/L, solar salt 20 g/L, $H_3BO_3$ 5.0 mg/L, $MnCl_2$ 3.0 mg/L, $CuSO_4$ 0.2 mg/L, $NaMo_4 \cdot 2H_2O$ 0.05 mg/L, $CoSO_4$ 0.05 mg/L, $ZnSO_4 \cdot 7H_2O$ 0.7 mg/L, and vitamin mixed solution 10 ml/L). One kind of the microalgae, whose growth rate was fast and whose culture condition was not complicated, was finally selected, and fungus bodies were recovered. The forms of the selected strains were observed using an optical microscope (shown in FIG. 1). The selected fungus bodies were washed with a phosphate buffered solution (PBS, pH 7.5), and then dried in a dry oven at 55° C. for 16 hours to obtain dry fungus bodies.

The 18s rRNA gene sequence was analyzed for the molecular identification of strains of the finally selected microalgae. DNA is separated from the purely separated colonies of the selected species, and then 18s rRNA was amplified by polymerase chain reaction (PCR) using primers for gene amplification in a 18s rRNA region. The primers for gene amplification are summarized in Table 1 below.

TABLE 1

| Primer | Sequence (5'-3') | SEQ ID NO. |
|---|---|---|
| 18s-001F | AACCTGGTTGATCCTGCCAGTA | 2 |
| 18s-013R | CCTTGTTACGACTTCACCTTCCTCT | 3 |

In this case, after denaturation at 95° C. for 5 minutes, the PCR was carried out for a total of 25 cycles under the following conditions: denaturation at 95° C. for 30 seconds; annealing at 52° C. for 30 seconds; and polymerization at 72° C. for 1 minute and 30 seconds. Thereafter, the polymerization reaction was carried out at 72° C. for 7 minutes.

As a result of analyzing the nucleotide sequence using the amplified reaction solution, nucleotide sequence 1 (SEQ ID NO. 1) having a size of about 1792 bp was obtained. As a result of NCBI BLAST search, it was found that the nucleotide sequence 1 had about 99% homology with the previously reported strains of *Thraustochytrium* genus and had about 84% homology with strains of *Aurantiochytrium* genus and *Schizochytrium* genus.

Figure 2:
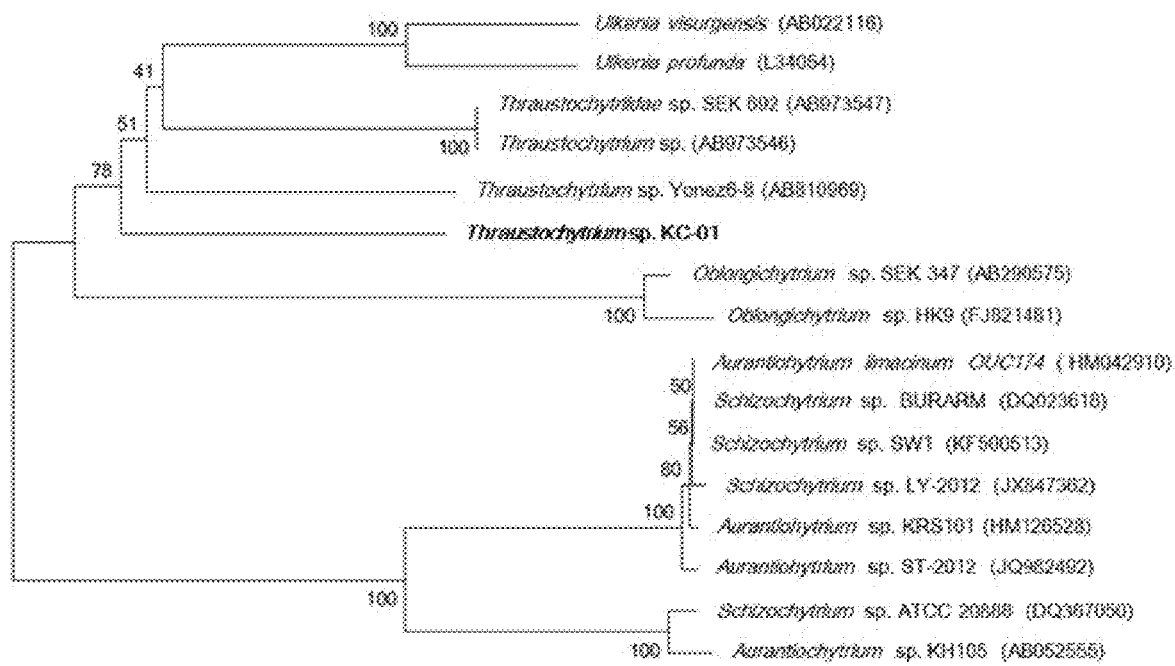
FIG. 2 shows a phylogenetic tree among KC01 strains of *Thraustochytrium* genus, strains of *Thraustochytrium* genus, strains of *Aurantiochytrium* genus, and strains of *Schizochytrium* genus.

Thus, phylogenetic tree among strains are expressed, and the results thereof are shown in FIG. 2. The corresponding strains were identified as microalgae of *Thraustochytrium* genus of Thraustochytrid family, and were thus named as KC01 of *Thraustochytrium* genus.

Example 2: Development of Mutant Microalgae

Example 2-1: Selection of Mutant Microalgae Through an Artificial Mutation Method In the present disclosure, the following experiment was carried out so as to separate strains having improved productivity of docosahexaenoic acid (DHA) by gamma ray irradiation mutation of the KC01 strains of *Thraustochytrium* genus, which were separated in Example 1.

Specifically, the KC01 strains of *Thraustochytrium* genus were cultured in a GYEP culture medium (glucose 2%, peptone 1%, yeast extract 0.5%, and solar salt 2%) for 24 hours to activate the strains. The activated strains were inoculated into a subculture medium (glucose 5%, peptone 1%, yeast extract 0.5%, and solar salt 2%) having been sterilized at 121° C. for 15 minutes and cultured for 14 hours, and then fungus bodies were recovered. The recovered fungus bodies were suspended in 50 mL of a PBS buffer, irradiated with gamma rays at a dose of 1 to 5 kGy for 1 hour, and then cultured in 50 mL of a basic culture medium (glucose 5%, peptone 1%, yeast extract 0.5%, and solar salt 2%) using a 500 mL flask at a temperature of 28° C. and a revolution of 120 rpm for 2 days. Then, the suspended fungus bodies were appropriately diluted when the death rate is 99%, and subcultured in a GYEP flat plate culture medium (glucose 2%, peptone 1%, yeast extract 0.5%, and solar salt 2%, agar 2%, pH 7.0) two times.

Primarily, colonies, whose color becomes white, were selected in order to select strains predicted to have reduced sulfated pigments produced in addition to oils containing polyunsaturated fatty acids. The mutant strains obtained by the above method were named as CJM01 strains of *Thraustochytrium* genus, deposited on May 30, 2018 with the Korean Collection for Type Cultures (KCTC), an international depository organization under the Budapest Treaty, and granted the deposit number KCTC 13538BP.

Example 2-2: Analysis of Abilities of Newly Separated Microalgae and Mutant Strains to Produce Oil Containing Polyunsaturated Fatty Acids The CJM01 and KC01 strains selected from Example 2-1 were cultured as follows in order to compare the ability of CJM01 strains to produce oil containing polyunsaturated fatty acids with the ability of KC01 strains to produce oil containing polyunsaturated fatty acids.

Specifically, in order to culture the CJM01 and KC01 strains, which are microalgae of *Thraustochytrium* genus according to the present disclosure, the CJM01 and KC01 strains were cultured in MJW01 culture medium (glucose 30 g/L, $MgSO_4 \cdot 7H_2O$ 3.0 g/L, $Na_2SO_4$ 10 g/L, NaCl 1.0 g/L, yeast extract 9.0 g/L, $MSG \cdot 1H_2O$ 1.0 g/L, $NaNO_3$ 1.0 g/L, $KH_2PO_4$ 0.1 g/L, $K_2HPO_4$ 0.5 g/L, $CaCl_2$ 0.5 g/L, and vitamin mixed solution 10 ml/L) under basic culture medium conditions of 28° C., 300 rpm, 1 vvm, and pH 7.5 for 4 days. Fungus bodies were recovered by centrifugation, washed with a PBS buffer three times, and then dried at 55° C. for 12 hours to measure the weight of the fungus bodies.

The content of docosahexaenoic acid-containing oil utilizing the dried fungus bodies was measured as follows. Specifically, 8.3 M of hydrochloric acid solution was applied to 2 g of the dried fungus bodies to hydrolyze the cell walls of fungus bodies of microalgae at 80° C., 30 mL of ethyl ether and 20 mL of petroleum ether were added to the dried fungus bodies and stirred for 30 seconds, and then the mixture was centrifugally separated 3. This procedure was repeated three times or more. Then, the separated solvent layer was recovered, put into a round flask whose weight had been previously measured, purged with nitrogen to remove a solvent, and then the resultant was put into a container, whose moisture had been removed, and dried. The weight of the dried oil was measured to calculate the total oil content. The content of DHA in the oil was measured by chromatography after pretreating the oil with 0.5 N methanolic NaOH and 14% trifluoroborane methanol ($BF_3$).

The culture performance of the KC01 strains of *Thraustochytrium* genus, cultured by the above method, and the culture performance of the CJM01 mutant strains selected by gamma ray irradiation are given in Tables 2 and 3. It was found from Tables 2 and 3 that DHA, which is highly functional omega-3 oil, was produced.

The "biomass" in Tables 2 and 3 refers to the concentration of the fungus bodies in a culture solution, and may be used in combination with dry cell weight (DCW). The content of DHA is expressed as the content thereof with respect to biomass or total fatty acid (TFA).

As shown in the following results, the production of DHA by the CJM01 mutant strains was found to be improved as compared with that by parent strains (KC01 strains of *Thraustochytrium* genus) (see Tables 2 and 3). Specifically, the production of DHA by the CJM01 mutant strains was increased by about 1.3 times as compared with that by the KC01 strains. Further, it was found that the productivity of DHA by the CJM01 mutant strains was increased by about 1.7 times as compared with that by the KC01 strains because culturing time was significantly shortened without a decrease in the obtained fungus bodies.

TABLE 2

Content and productivity of docosahexaenoic acid (DHA) according to culturing of KC01 parent strains *Thraustochytrium* genus

| Entry | Time (hr) | Biomass g/L | DHA (%/Biomass) | DHA (%/TFA) | Lipid % | DHA Productivity (g/l/h) |
|---|---|---|---|---|---|---|
| 1 | 71.5 | 115.2 | 22.7 | 35.6 | 63.7 | 0.365 |
| 2 | 73.0 | 127.5 | 21.6 | 33.6 | 64.3 | 0.377 |
| 3 | 78.5 | 141.8 | 22.3 | 36.8 | 60.5 | 0.402 |
| Avg. | 74.3 | 128.2 | 22.2 | 35.3 | 62.8 | 0.381 |

TABLE 3

Content and productivity of docosahexaenoic acid (DHA) according to culturing of CJM01 mutant strains *Thraustochytrium* genus

| Entry | Time (hr) | Biomass g/L | DHA (%/Biomass) | DHA (%/TFA) | Lipid % | DHA Productivity (g/l/h) |
|---|---|---|---|---|---|---|
| 1 | 57.3 | 123.0 | 29.3 | 47.6 | 61.5 | 0.629 |
| 2 | 55.5 | 133.5 | 27.5 | 45.5 | 60.4 | 0.661 |
| 3 | 54.8 | 133.5 | 28.0 | 57.1 | 49.0 | 0.682 |
| Avg | 55.9 | 130.0 | 28.3 | 50.1 | 57.0 | 0.657 |

From the above results, it was found that the CJM01 strains, which are mutant strains, had an increased DHA content and improved DHA conductivity as compared with the KC01 strains, which are parent strains.

Example 2-3: Analysis of Abilities of Newly Separated Microalgae and Mutant Strains to Produce Amino Acids In order to evaluate the culture characteristics of CJM01 strains, the total content of amino acids in the above culture solution was determined.

Specifically, 10 mL of sample was collected from each of the above culture solutions, diluted with distilled water by 20 times, and filtered, and then the total content of amino acids was analyzed using liquid chromatography. As the result of analyzing the total concentration of amino acids, aspartate, serine, glutamate, glycine, alanine, valine, methionine, isoleucine, leucine, tyrosine, phenylalanine, lysine, and arginine were respectively detected in the culture solution of the KC01 parent strains in an amount of 10 mg/L, whereas most of amino acids were not detected in the culture solution of the CJM01 strains having an improved DHA content.

Specifically, it was found that, in the case of the CJM01 mutant strains, the total concentration of amino acids as side products other than DHA is reduced by about 99% or more, as compared with the KC01 parent strains (see Table 4).

Thus, it was found that, in the case of the CJM01 mutant strains, the growth of fungus bodies is at an equivalent level, as compared with the KC01 parent strains, and the total content of lipids is not greatly reduced as compared with the content of fungus bodies, and thus the CJM01 mutant strains have used the supplied carbon source for a DHA biosynthetic mechanism more effectively as compared with the KC01 parent strains.

TABLE 4

Analysis of total amino acids in culture solution according to the culture of KC01 parent strains of *Thraustochytrium* genus and CJM01 mutant strains of *Thraustochytrium* genus

| Amino acid (mg/L) | T.KC01 parent strains | | | | T.CJM01 mutant strains | | | |
|---|---|---|---|---|---|---|---|---|
| | 1 | 2 | 3 | Avg | 1 | 2 | 3 | Avg |
| Asp | 20.3 | 28.9 | 12.3 | 20.5 | 0.0 | 0.0 | 0.0 | 0.0 |
| Ser | 49.5 | 85.2 | 28.6 | 54.4 | 0.0 | 0.0 | 0.0 | 0.0 |
| Glu | 91.6 | 108.4 | 193.0 | 131.0 | 0.0 | 0.0 | 0.0 | 0.0 |
| Gly | 32.4 | 52.8 | 28.7 | 38.0 | 0.0 | 0.0 | 0.0 | 0.0 |
| Ala | 72.6 | 104.4 | 41.1 | 72.7 | 0.0 | 0.0 | 0.0 | 0.0 |
| Val | 83.0 | 130.8 | 59.5 | 91.1 | 10.1 | 0.0 | 0.0 | 3.4 |
| Met | 32.1 | 58.2 | 16.0 | 35.4 | 0.0 | 0.0 | 0.0 | 0.0 |
| Ile | 42.1 | 77.0 | 18.8 | 46.0 | 0.0 | 0.0 | 0.0 | 0.0 |
| Leu | 93.0 | 166.9 | 41.8 | 100.6 | 0.0 | 0.0 | 0.0 | 0.0 |
| Tyr | 51.7 | 86.5 | 0.0 | 46.1 | 0.0 | 0.0 | 0.0 | 0.0 |
| Phe | 83.4 | 129.9 | 58.4 | 90.5 | 0.0 | 0.0 | 0.0 | 0.0 |
| Lys | 45.9 | 83.3 | 20.2 | 49.8 | 0.0 | 0.0 | 0.0 | 0.0 |
| His | 15.9 | 25.0 | 0.0 | 13.6 | 0.0 | 0.0 | 0.0 | 0.0 |
| Arg | 57.0 | 93.7 | 24.0 | 58.2 | 0.0 | 0.0 | 0.0 | 0.0 |
| Sum | 770.5 | 1231.1 | 542.5 | 848.0 | 10.1 | 0.0 | 0.0 | 3.4 |

Example 3: Optimization of Culture Medium Conditions

In order to further improve the content and productivity of DHA using the CJM01 strains having a reduced amino acid content and an improved DHA content, the strains having been selected from Example 2, culture medium conditions were optimized.

Specifically, based on the MJW01 culture medium used in Example 2-2, in order to increase the content of nitrogen sources in the culture medium and reduce production costs, the concentration of yeast extract as an organic nitrogen source was decreased, $(NH_4)_2SO_4$ as an inorganic nitrogen source was added, and the concentration of $NaNO_3$ was increased to convert the MJW01 culture medium into an MJW02 culture medium (glucose 30 g/L, $MgSO_4 \cdot 7H_2O$ 5.0 g/L, $Na_2SO_4$ 3 g/L, NaCl 0.5 g/L, yeast extract 1.0 g/L, $MSG \cdot 1H_2O$ 1.0 g/L, $NaNO_3$ 8.0 g/L, $(NH_4)_2SO_4$ 3.0 g/L, $KH_2PO_4$ 0.1 g/L, $K_2HPO_4$ 0.5 g/L, $CaCl_2$ 0.1 g/L, and vitamin mixed solution 10 ml/L).

In order to compare the conditions of the MJW01 culture medium with the conditions of the MJW02 culture medium, CJM01 strains were respectively cultured in the above culture mediums. As a result, as shown in Table 5 below, the amount of fungus bodies was decreased as the concentration of yeast extract was decreased, but culturing time was significantly shortened with an increase of an inorganic nitrogen source. Consequently, it was found that the content of DHA in the MJW02 culture medium is equal to or more than the content of DHA in the MJW01 culture medium, and the productivity of DHA in the MJW02 culture medium was increased by 1.13 times with respect to the productivity of DHA in the MJW01 culture medium.

TABLE 5

Content and productivity of docosahexaenoic acid (DHA) according to culture medium conditions

| Culture medium conditions | Time (hr) | Biomass g/L | DHA (%/Biomass) | DHA (%/TFA) | Lipid % | Productivity (g/l/h) |
|---|---|---|---|---|---|---|
| MJW01 | 59.3 | 133.4 | 26.0 | 42.6 | 61.0 | 0.584 |
| MJW02 | 52.1 | 124.3 | 27.7 | 49.0 | 56.6 | 0.661 |

As described above, those skilled in the art will be able to understand that the present disclosure can be easily executed in other detailed forms without changing the technical spirit or an essential feature thereof. Therefore, it should be appreciated that the aforementioned embodiments are illustrative in all aspects and are not restricted. The scope of the present disclosure is represented by claims to be described below rather than the detailed description, and it is to be interpreted that the meaning and scope of the claims and all the changes or modified forms derived from the equivalents thereof come within the scope of the present disclosure.

The invention claimed is:

1. CJM01 microalgae deposited under accession No. KCTC 13538BP of *Thraustochytrium* genus.

2. The microalgae of claim 1, wherein the CJM01 microalgae of *Thraustochytrium* genus includes docosahexaenoic acid in an amount of 40 wt % to 60 wt % based on a total weight of fatty acids.

3. The microalgae of claim 1, wherein the CJM01 microalgae of *Thraustochytrium* genus has a docosahexaenoic acid productivity of 0.5 to 0.7 g/l/h.

4. A method of producing a biomass, comprising:
culturing the CJM01 microalgae deposited under accession No. KCTC 13538BP of *Thraustochytrium* genus of claim 1; and recovering a biomass containing docosahexaenoic acid from the microalgae, a cultured product thereof, a dried product thereof, or a pulverized product thereof.

5. The method of claim 4, wherein the culturing is performed under heterotrophic conditions.

6. The method of claim 4, wherein the culturing is performed using a culture medium including a carbon source and a nitrogen source.

7. The method of claim 6, wherein the carbon source is at least one selected from the group consisting of glucose, fructose, maltose, galactose, mannose, sucrose, arabinose, xylose, and glycerol.

8. The method of claim 6, wherein the nitrogen source is i) an organic nitrogen source selected from the group consisting of a yeast extract, a beef extract, peptone, and tryptone, or ii) inorganic nitrogen source selected from the group consisting of ammonium acetate, ammonium nitrate, ammonium chloride, ammonium sulfate, sodium nitrate, urea, and monosodium glutamate (MSG).

9. A method of producing a bio-oil, comprising: culturing the CJM01 microalgae deposited under accession No. KCTC 13538BP of *Thraustochytrium* genus of claim 1; and recovering a lipid containing docosahexaenoic acid (DHA) from the microalgae, a cultured product thereof, a dried product thereof, or a pulverized product thereof.

\* \* \* \* \*